United States Patent
Klopsch et al.

(10) Patent No.: US 9,765,238 B2
(45) Date of Patent: Sep. 19, 2017

(54) COATING COMPOSITIONS COMPRISING A COMPOUND WITH AT LEAST TWO CYCLIC CARBONATE GROUPS AND A SILOXANE GROUP

(71) Applicant: BASF SE, Ludwigshafen (DE)

(72) Inventors: Rainer Klopsch, Worms (DE); Andreas Lanver, Mannheim (DE); Christina Haaf-Kleinhubbert, Hemsbach (DE); Verena Mormul, Mannheim (DE); Volker Hickmann, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/906,208

(22) PCT Filed: Jul. 11, 2014

(86) PCT No.: PCT/EP2014/064903
§ 371 (c)(1),
(2) Date: Jan. 19, 2016

(87) PCT Pub. No.: WO2015/010924
PCT Pub. Date: Jan. 29, 2015

(65) Prior Publication Data
US 2016/0186008 A1     Jun. 30, 2016

(30) Foreign Application Priority Data
Jul. 22, 2013   (EP) ..................................... 13177411

(51) Int. Cl.
| | |
|---|---|
| *C08L 83/06* | (2006.01) |
| *C09D 183/06* | (2006.01) |
| *C08G 77/38* | (2006.01) |
| *C07F 7/08* | (2006.01) |
| *C09D 201/08* | (2006.01) |
| *C09D 133/14* | (2006.01) |
| *C08G 77/20* | (2006.01) |
| *C08G 77/14* | (2006.01) |

(52) U.S. Cl.
CPC .......... *C09D 183/06* (2013.01); *C07F 7/0852* (2013.01); *C08G 77/38* (2013.01); *C09D 133/14* (2013.01); *C09D 201/08* (2013.01); *C08G 77/14* (2013.01); *C08G 77/20* (2013.01); *C08G 2150/00* (2013.01); *C08L 83/06* (2013.01)

(58) Field of Classification Search
None
See application file for complete search history.

(56) References Cited

U.S. PATENT DOCUMENTS

2015/0232700 A1\*  8/2015  Frances ................ C09D 183/06
                                                          522/31

FOREIGN PATENT DOCUMENTS

| EP | 0 837 062 A1 | 4/1998 |
|---|---|---|
| JP | 2013043398 A \* | 3/2013 |
| WO | WO 2011/157671 A1 | 12/2011 |
| WO | WO 2013/144299 A1 | 10/2013 |

OTHER PUBLICATIONS

International Search Report and Written Opinion issued Sep. 25, 2014 in PCT/EP2014/064903 filed Jul. 11, 2014 (with English language translation).
Zhenya Zhu, et al., "Synthesis of Polysiloxanes Bearing Cyclic Carbonate Side Chains. Dielectric Properties and Ionic Conductivities of Lithium Triflate Complexes" Macromolecules, vol. 27, No. 15, XP055135538, 1994, pp. 4076-4079.
Andrea K. Buzas, et al., "Gold-catalyzed rearrangement of propargylic *tert*-butyl carbonates" Tetrahedron, vol. 65, 2009, pp. 1889-1901.

\* cited by examiner

*Primary Examiner* — Richard A Huhn
(74) *Attorney, Agent, or Firm* — Oblon, McClelland, Maier & Neustadt, L.L.P.

(57) ABSTRACT

Coating compositions comprising a compound having at least two cyclic carbonate groups and a siloxane group (called "carbonate compound").

21 Claims, No Drawings

COATING COMPOSITIONS COMPRISING A COMPOUND WITH AT LEAST TWO CYCLIC CARBONATE GROUPS AND A SILOXANE GROUP

The invention relates to coating compositions comprising a compound having at least two cyclic carbonate groups and a siloxane group, which in this specification is called "carbonate compound". The invention also relates to specific carbonate compounds.

In coating compositions reactive binder systems frequently find use. Reactive binder systems consist in general of two components. The two components are typically liquid at room temperature and can easily be processed. Only in the subsequent use do the two components react with one another to form a polymer or even a crosslinked polymer, which gives the resultant coating composition the desired qualities, such as hardness, elasticity, and resistance toward solvents or chemicals.

Long-established are reactive binder systems comprising compounds having at least two isocyanate groups (polyisocyanates for short) and compounds having at least two hydroxyl groups (polyols for short). In the context of their use, polyisocyanates and polyols react to form a polyurethane.

Also long-established are reactive binder systems composed of compounds having at least two isocyanate groups (polyisocyanates for short) and compounds having at least two primary or secondary amino groups (polyamines for short). In the context of their use, polyisocyanates and polyamines react to form a polyurea.

Polyisocyanates are highly reactive and react very easily with water. On account of this sensitivity to moisture, the absence of water must be ensured in the storage and use of polyisocyanates. In coating compositions, aromatic polyisocyanates may lead to discoloration. Furthermore, there might also be health concerns about specific, highly volatile polyisocyanates.

In principle, therefore, there is a desire for alternative binder systems which do not include polyisocyanates.

Described in Macromolecules 1995, 27, 4076-4079 are compounds having two or more carbonate groups and a polysiloxane group. The compounds are prepared by hydrosilylation. A possible use of the compounds in capacitors or batteries is mentioned.

WO 2011/157671, EP-A 837062 and Tetrahedron 65 (2009) 1889-1901 likewise disclose compounds with a cyclic carbonate group and their preparation. These compounds correspond to the compounds of the formula IV later on.

WO 2011/157671 describes the use of these compounds as reactive diluents in epoxy resins.

According to patent application PCT/EP2013/056716 (PF 73287), the compounds of the formula IV are reacted to form polymerizable compounds with an ethylenically unsaturated group in the radical R4. The new monomers obtained are radically polymerizable. PCT/EP2013/056716 describes the preparation of homopolymers and copolymers by radical polymerization. The resultant polymers also find use in two-component binder systems.

An object of the present invention were coating compositions which can be used alternatively to coating compositions based on polyisocyanates. The coating compositions are to be suitable for producing coatings having good, balanced performance qualities. The coatings are to exhibit high hardness in conjunction with high elasticity. The resistance toward solvents and chemicals they exhibit is also to be high.

The coating compositions defined above have been found accordingly. Also found have been specific compounds having at least two cyclic carbonate groups and a siloxane group (carbonate compounds), which are especially suitable for coating compositions.

The coating compositions comprise the carbonate compound defined above. The term "carbonate compound" also encompasses mixtures of different carbonate compounds, unless anything different is apparent from the context hereinbelow.

The Carbonate Compound:

The cyclic carbonate groups of the carbonate compound are preferably 5-membered rings formed of 3 C atoms and 2 oxygen atoms. The C atom between the two oxygen atoms is substituted by oxygen (carbonate group); the 5-membered ring is closed by an ethylene group between the two oxygen atoms, and the ethylene group may be substituted on both C atoms. The carbonate group is bonded to the compound via one of the two C atoms of the ethylene group.

The carbonate compound contains preferably 2 to 50, more particularly 2 to 30 cyclic carbonate groups, and very preferably 2 to 20 cyclic carbonate groups.

The carbonate compound further contains a siloxane group. In siloxane groups, the silicon atoms are bonded not directly but via oxygen atoms. Siloxane groups may be linear or branched. The siloxane group contains preferably 2 to 100 Si atoms, more particularly 2 to 70 Si atoms, and very preferably 2 to 50 Si atoms, in particular, for example, also 2 to 20 Si atoms. The Si atoms, unless bonded to oxygen atoms or to the carbonate groups, are substituted by hydrogen or organic groups. The above organic groups are, in particular, hydrocarbon groups, and more preferably C1 to C10 and more particularly C1 to C4 alkyl groups. In one particular embodiment the Si atoms only contain small amounts of hydrogen as substituent. In particular there is less than 30 mol %, more particularly less than 20 mol %, very preferably less than 10 mol % of hydrogen substituents on the Si atoms. In one special embodiment there is less than 5%, more particularly less than 1 mol %, of hydrogen substituents on the Si atoms.

In one particular embodiment the siloxane groups are bonded via organic groups, more particularly alkylene groups, to the cyclic carbonate groups; examples of groups contemplated as above alkylene groups include C2 to C10 alkylene groups, more particularly C2 to C4 alkylene groups, and very preferably an ethylene group, as linking member between the siloxane group and the cyclic carbonate group.

Carbonate compounds of these kinds that are contemplated include, for example, the compounds with cyclic carbonate groups and a siloxane group that are described in Macromolecules 1994, 27, 4076-4079.

In one preferred embodiment the above-described carbonate compound is a compound of the formula I

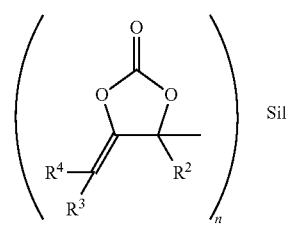

or a compound of the formula II

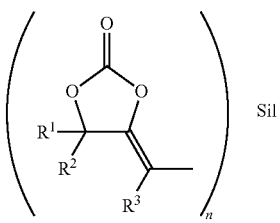

In formula I and II, Sil in each case is an n-valent radical with a siloxane group of 2 to 100 Si atoms, preferably of 2 to 70, more particularly of 2 to 50 Si atoms. In one particularly preferred embodiment, Sil is in each case an n-valent radical with a siloxane group of 2 to 20 and particularly 2 to 10 Si atoms. Besides the siloxane group, the Sil group may also contain organic bridge groups for attaching the siloxane group to the carbonate group. The bridge groups are preferably alkylene groups, more particularly C2 to C10 alkylene groups, very preferably C2 to C5 alkylene groups, and more particularly a C2 alkylene group. Sil more particularly is an n-valent radical consisting of a siloxane group as set out above and n bridge groups in accordance with n attached carbonate groups.

The variable n indicates the number of carbonate groups. In accordance with the statements above, n is an integer from 2 to 50, more particularly an integer from 2 to 30, and preferably an integer from 2 to 20. In one particularly preferred embodiment n is an integer from 2 to 5. Very preferably, for example, n is 2 or 3.

The radicals $R^1$ to $R^4$ (radicals $R^2$ to $R^4$ in formula I and $R^1$ to $R^3$ in formula II) are in each case independently of one another hydrogen or an organic group having 1 to 10 C atoms. The above organic group is preferably a hydrocarbon group, more particularly an alkyl group. The radicals $R^1$ to $R^4$ are preferably in each case independently of one another hydrogen or a C1 to C10 alkyl group, and more particularly are independently of one another a hydrogen or a C1 to C4 alkyl group.

In one particular embodiment the radicals $R^1$ and $R^2$ (in formula I only radical $R^2$) are a C1-C4 alkyl group, more particularly a methyl group, and $R^3$ and $R^4$ (in formula II only $R^3$) are in each case a hydrogen.

Particularly preferred is the carbonate compound of the formula I.

A particularly preferred carbonate compound of the formula I is for example the compound of the formula III

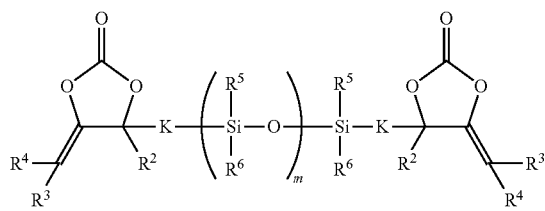

where $R^2$ to $R^4$ have the above definition, K is a divalent organic group having 2 to 10 C atoms, $R^5$ and $R^6$ independently of one another are a hydrogen atom or an organic group having 1 to 10 C atoms, and m is an integer from 1 to 99.

$R^2$ to $R^4$ otherwise have the above preferred definitions.

The preferred definitions of m correspond to the above number of preferred silicon atoms of the siloxane group, m being preferably an integer from 1 to 69, more preferably from 1 to 49, and more particularly from 1 to 19.

$R^5$ and $R^6$ are subject to all of the above statements concerning the preferred substituents on the silicon atoms. Very preferably, therefore, $R^5$ and $R^6$ are C1 to C4 alkyl groups or hydrogen, with preferably less than 30 mol %, more particularly less than 20 mol %, and very preferably less than 10 mol % of the substituents on the Si atoms being hydrogen; in one particular embodiment less than 5%, more particularly less than 1 mol %, of the substituents on the Si atoms are hydrogen.

The preparation of the carbonate compound

The carbonate compounds can be obtained by hydrosilylation. For this purpose a cyclic carbonate which is substituted on one of the ring atoms by an ethylenically unsaturated group (double or triple bond, preferably double bond, more preferably a vinyl group) (referred to below for short as "ethylenically unsaturated carbonate") can be reacted with a siloxane which contains silicon-bonded hydrogen atoms, i.e., reactive hydrogen atoms.

The reaction involves the addition of a reactive hydrogen atom at a C atom of the ethylenically unsaturated group and the addition of the remaining siloxane group at the other C atom of the ethylenically unsaturated group. The reaction scheme is reproduced on an exemplary basis in preparation example 2.

A corresponding preparation of carbonate compounds having two cyclic carbonate groups and a siloxane group by hydrosilylation is described for example by Macromolecules 1995, 27, 4076-4079.

In the hydrosilylation both the ethylenically unsaturated carbonate and the siloxane may be used in excess. For example, a siloxane may be selected which has the desired number of silicon-bonded hydrogens, and the desired amount of ethylenically unsaturated carbonate may be determined accordingly. With an equimolar amount of the ethylenically unsaturated carbonate, full conversion sees all of the silicon-bonded hydrogens being replaced by a substituent with the carbonate group. If less than the equimolar amount of ethylenically unsaturated carbonate is brought to the reaction, the resulting compound contains silicon-bonded hydrogens as well as the carbonate groups. In one preferred embodiment the ethylenically unsaturated carbonate is used on an equimolar basis or in excess. In this way the resulting compound contains no, or only a few, silicon-bonded hydrogen atoms.

The reaction may take place in the presence or absence of solvent. In general the starting materials used (ethylenically unsaturated carbonate and siloxane) are liquid, and so no solvent is required.

The hydrosilylation is carried out preferably in the presence of a catalyst. Suitable catalysts are, for example, metals or metal salts of the platinum group. They are preferably supported catalysts, where the metals are applied on a support of aluminum oxide or of zirconium dioxide, for example.

The reaction takes place in general under atmospheric pressure at temperatures of 20 to 100° C. The reaction is exothermic and therefore cooling is carried out to the extent necessary, to maintain the temperature within the desired range.

The carbonate compound obtained is often solid under standard conditions (20° C., 1 bar, room temperature). After the end of the reaction, the solid obtained may be purified by dissolving it in a suitable solvent, such as an aromatic or aliphatic hydrocarbon for example, and carrying out recrystallization.

Preferred carbonate compounds of the formula I or II are obtainable accordingly by hydrosilylation of a compound of the formula IV

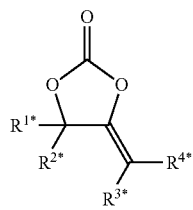

In formula IV the radicals R1* to R4* have the above definition of the corresponding radicals R1 to R4 in formula I and II, but one of the radicals R1* to R4* must contain an ethylenically unsaturated group.

The preparation of compounds of the formula IV is known and is described in for example Tetrahedron 65 (2009) 1889-1901.

The compound of the formula IV is reacted with a siloxane which contains the desired number of Si atoms and silicon-bonded hydrogens, but at least two silicon-bonded hydrogens.

In the case of the carbonate compounds of the formula I, hydrosilylation is carried out using a compound of the formula IV in which the radicals R1* to R4* have the above definition of the corresponding radicals R1 to R4 in formula I and II, but at least one of the radicals R1* or R2* contains an ethylenically unsaturated group, preferably a terminal ethylenically unsaturated group.

With particular preference, therefore, the compound of the formula IV is a compound in which R1* is a C2 to C10 alkenyl group or a C2 to C10 alkynyl group, R2* is a hydrogen atom or a C1 to C10 alkyl group, and R3* and R4* independently of one another are a hydrogen atom or a C1 to C10 alkyl group. More particularly R1* is a C2 to C10 alkenyl group, more particularly an alkenyl group with a terminal double bond. In one especially preferred embodiment R1* is a vinyl group.

In the case of particularly preferred carbonate compounds of the formula I, therefore, the hydrosilylation is carried out using more particularly a compound of the formula IV in which R1 * is a vinyl group, R2* is a C1 to C4 alkyl group, and R3* and R4* are an H atom. An example of such a compound of the formula IV is the compound of the formula V below:

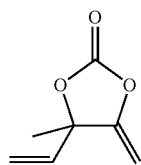

The coating compositions

Coating compositions comprise as an essential constituent a binder, which forms the coherent coating and which gives the coating its mechanical strength. Coating compositions often consist exclusively of the binder. They may, however, also include additives, examples being pigments, dyes, stabilizers, etc., which impart additional properties to the coating, such as color, stability toward aging and discoloration, etc.

The coating compositions comprise the above carbonate compounds as a constituent of the binder.

On account of the alkylidene-1,3-dioxolan-2-one groups they contain, the carbonate compounds are able to react with numerous nucleophilic groups, with formation of bonds. Examples of such nucleophilic groups are, for example, hydroxyl groups, primary and secondary amino groups, phosphine groups, phosphonate groups, and mercapto groups.

Besides the carbonate compounds, therefore, the binder of the coating compositions preferably includes a compound which can be reacted with the carbonate compounds to form a relatively high molecular mass and/or crosslinked polymer system and, in association therewith, a coating having good mechanical qualities. As well as the carbonate compounds, therefore, the coating compositions preferably comprise a compound having at least two reactive groups selected from hydroxyl groups, primary amino groups, secondary amino groups, and mercapto groups; such compounds are called "reactive compound" below.

With particular preference the reactive compounds are compounds having at least two hydroxyl groups or at least two primary or secondary amino groups. In one preferred embodiment the hydroxyl groups or primary or secondary amino groups are each attached by an aliphatic group, and are therefore what are called aliphatic hydroxyl groups, or aliphatic primary or secondary amino groups, respectively.

Compounds having two or more hydroxyl groups are called "polyols" below. Compounds having at least two primary or secondary amino groups are called polyamines below.

With particular preference, therefore, as well as the carbonate compound, the coating compositions comprise polyols, polyamines, or mixtures thereof.

Both low molecular mass and relatively high molecular mass polyols or polyamines are contemplated as a constituent of the coating compositions.

Low molecular mass polyols are, for example, aliphatic polyols or ether group-containing aliphatic polyols having 2 to 5 hydroxyl groups such as 1,4-butanediol, ethylene glycol, diethylene glycol, triethylene glycol, neopentyl glycol, 1,3-propanediol, 1,5-pentanediol, 1,6-hexanediol, glycerol, diglycerol, pentaerythritol, dipentaerythritol, and sugar alcohols such as sorbitol and mannitol.

Low molecular mass polyamines are, for example, aliphatic polyamines having 2 to 5 primary or secondary amino groups such as ethylenediamine, 1,2- and 1,3-propanediamine, neopentanediamine, hexamethylenediamine, diethylenediamine, triethylenetetramine, tetraethylenepentamine, trimethylhexamethylenediamine, 1,2-diaminocyclohexane, or isophoronediamine.

The low molecular mass polyols or polyamines have in particular a molecular weight of 60 to 499 g/mol.

Higher molecular mass polyols or polyamines are, in particular, polyester polyols, polyether polyols, polyesteramide polyols, polycarbonate polyols, polyacrylate polyols, polyetheramines, polyamidoamines, or mixtures thereof.

The above polyols and polyamines are long-established and have to date been used for purposes including coating compositions comprising polyisocyanates. They are obtainable in particular by reaction of low molecular mass polyols with dicarboxylic acids (polyester polyols), with dicarboxylic acids and/or dicarboxamides (polyester amide polyols), with carbonates (polycarbonate polyols), by alkoxylation of low molecular mass polyols (polyether polyols), or by amination of the above polyols, more particularly the polyether polyols, to form polyamines (polyetheramines).

Polyamidoamines are obtainable by reaction of dimeric fatty acids (e.g., dimeric linoleic acid) with low molecular mass polyamines.

Polyacrylate polyols are obtainable by radical polymerization of (meth)acrylates, with hydroxyl-functional (meth)acrylates being used as comonomers.

The relatively high molecular mass polyols and polyamines preferably have a number-average molecular weight of 500 to 10 000 g/mol, more particularly 800 to 5000 g/mol (determined by gel permeation chromatography).

The coating compositions comprise the carbonate compounds and the reactive compounds more particularly in an amount such that the molar ratio of the cyclic carbonate groups to the groups reactive therewith (more particularly hydroxyl groups, primary and secondary amino groups) is in the range from 1:10 to 10:1, more particularly in the range from 5:1 to 1:5, and very preferably in the range from 1:2 to 2:1. In one particular embodiment the above molar ratio is 1:1.5 to 1.5:1, more particularly 1:1.2 to 1.2:1.

As well as the carbonate compounds and reactive compounds, the coating compositions may comprise further constituents.

Examples of those contemplated include catalysts, which are used especially in the case of polyols as reactive compound and which catalyze the reaction of the hydroxyl groups with the cyclic carbonate groups. Catalysts of this kind are, in particular, compounds having nitrogen atoms, more particularly amino compounds or aza compounds such as DBU (1,8-diazabicyclo[5.4.0]undec-7-ene). The amount of such catalysts may for example be 0.01 to 10 parts by weight, more particularly 0.1 to 5 parts by weight, per 100 parts by weight, based on the sum total weight of carbonate compounds and polyols.

As a further constituent, the coating compositions may comprise solvents. Solvents are, in particular, water and organic compounds which are liquid at 20° C. (1 bar), which do not react with constituents of the binder, and which are removed on later formation of the coating. The accompanying use of solvent may be contemplated especially in the case of solid carbonate compounds. These compounds can be dissolved in the solvent, butyl acetate for example, and mixed easily, in the form of the solution, with the other constituents of the coating composition. The solvents also lower the viscosity of the coating composition and facilitate the coating operation.

Polar or nonpolar solvents are among solvents contemplated. Nonpolar solvents include aliphatic or aromatic hydrocarbons. Preferred solvents are polar organic solvents, more particularly ketones, ethers, or esters.

In particular, besides the carbonate compounds and the compounds reactive therewith, the coating compositions may further comprise other binders or binder constituents, examples being other polymers which form a coating, or low molecular mass compounds, examples being reactive diluents, which are attached to the other polymers or which contribute by curing to the formation of the coating.

In one preferred embodiment the carbonate compounds and the compounds reactive therewith are the predominant and essential constituent of the coating compositions or of the binder of the coating compositions.

Preferably at least 50 wt %, more preferably at least 70 wt %, very preferably at least 90 wt %, and, in one particular embodiment, at least 95 wt % or 100 wt % of all of the constituents of the binder of the coating composition are carbonate compounds and compounds reactive therewith.

Further constituents of the coating composition may be, for example, auxiliaries, of the kind useful or customary for the specific use of the coating composition. The coating compositions may for example be adhesives or paints.

Examples of customary auxiliaries in the case of the adhesives are tackifying resins (tackifiers).

Examples of other auxiliaries for adhesives or paints are organic or inorganic fillers in the form of small particles or fibers such as calcium carbonates, silicates, glass fibers, or carbon fibers.

Examples of further auxiliaries contemplated include antioxidants, UV absorbers/light stabilizers, metal deactivators, antistats, reinforcing agents, fillers, antifogging agents, propellants, biocides, plasticizers, lubricants, emulsifiers, colorants, pigments, rheological agents, impact tougheners, optical brighteners, and flame retardants.

The coating compositions contain preferably 0.1 to 50 wt %, more preferably 1 to 50 wt %, more particularly 5 to 50 wt % of carbonate compounds, based on the overall coating composition.

The coating compositions preferably comprise carbonate compounds and reactive compounds in a total amount of at least 10 wt %, more preferably of at least 30 wt %, more particularly of at least 50 wt %, and, in one particular embodiment, at least 70 wt %. The coating compositions may consist to an extent, for example, of 50 to 100 wt %, and more particularly of 70 to 100 wt %, of the carbonate compounds and the reactive compounds.

The coating compositions may be one-component or two-component coating compositions. One-component coating compositions contain carbonate compounds and the reactive compound as early as during the storage, up to the time of their subsequent use. In the case of two-component coating compositions, the constituents reactive with one another, in this case the carbonate compound and the reactive compound, are first of all stored separately and are not brought together until shortly before their use, to form the complete coating composition. The coating composition is preferably a two-component coating composition in which the carbonate compound and the reactive compound are brought together shortly before use and are optionally mixed with other constituents to form a homogeneous coating composition.

The coating compositions may for example be adhesives. Adhesives include, in particular, two-component structural adhesives. Structural adhesives serve for permanent joining of shaped parts to one another. The shaped parts may be of any desired material; materials contemplated include plastic, metal, wood, leather, ceramic, etc. The compositions may also be flooring adhesives. They are also suitable as adhesives for the production of circuit boards (electronic circuits), including in particular in accordance with the SMT method (surface mounted technology).

The coating compositions are more particularly paints, which here refers to coating compositions for producing coatings for protection from external exposures (e.g., corrosion control, protection from mechanical damage, from sunlight, or environmental effects, etc.), or coating compositions for decorative purposes (gloss varnishes, etc.). The paints may be applied by customary application techniques such as spraying, knife coating, brushing, pouring, dipping, or rolling, for example. Preference is given to employing spray application techniques such as, for example, compressed air spraying, airless spraying, high-speed rotation, and electrostatic spray application (ESTA), optionally in conjunction with hot spray application such as hot air spraying, for example.

The coating compositions may also be base coat or topcoat materials of multicoat paint systems.

With the paints it is possible to coat customary substrates or customary surfaces, examples being substrates or surfaces of metal, plastic, wood, ceramic, stone, textile, leather, glass, and also fiber composites, glass fibers, glass wool and rock wool, minerals, and construction materials such as plasterboard panels, cement fiberboard panels, or roofing shingles.

As adhesive or paint, for example, the coating compositions are first applied to the substrates that are to be coated, followed preferably by the reaction of the carbonate compound with the reactive compound (curing).

The curing of the coating composition may take place thermally by means of heating. Heating at the same time removes any accompanying solvent used.

The curing temperature may for example be 20 to 200° C., more particularly 50 to 200° C., very preferably 70 to 150° C. Curing may also take place at lower temperatures over a correspondingly greater time period.

The coatings obtained with the coating compositions of the invention have very good performance qualities. In particular they exhibit very good hardness in conjunction with good elastic qualities.

The coating compositions of the invention are easy to process. They are very reactive, and so are easy to cure under moderate conditions, though on the other hand they have a sufficiently long pot life, which facilitates the preparation of the coating composition by mixing of the constituents, and the coating operation.

EXAMPLES

Preparation Examples

Preparation Example 1

Preparation of 4-methyl-4-vinyl-5-methylene-1,3-dioxolan-2-one (Compound of the Formula IV, for Short: exoVCA)

Reaction scheme:

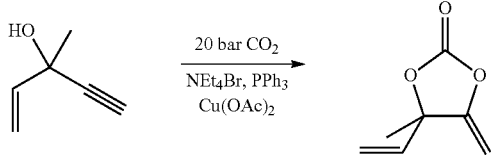

A 300 ml autoclave is charged with 3-methylpent-1-ene-4-yn-3-ol (100.00 g, 1.04 mol), triphenylphosphane (2 g, 8 mmol), tetraethylammonium bromide (2 g, 8 mmol) and copper(II) acetate (0.5 g, 2.8 mmol). The mixture is then heated to 75° C. and 20 bar of $CO_2$ are injected. The mixture is stirred at 75° C. for 15 hours, then cooled to room temperature and let down to atmospheric pressure. This batch is run a total of nine times, and the combined reaction discharges are jointly distilled (conditions: 10 mbar, bath temperature 100° C., 20 cm Vigreux column. The product goes over at a temperature of about 68° C.). This gives 1042 g (79%) of product with a purity of 98.5% (GC area %).

NMR analysis: conforms to the analysis indicated in the literature (e.g., in Tetrahedron 65 (2009) 1889-1901).

Preparation Example 2

Preparation of a Compound of Formula 1 from tetramethyldisiloxane and exoVCA (for Short: Si-V 1)

Reaction scheme:

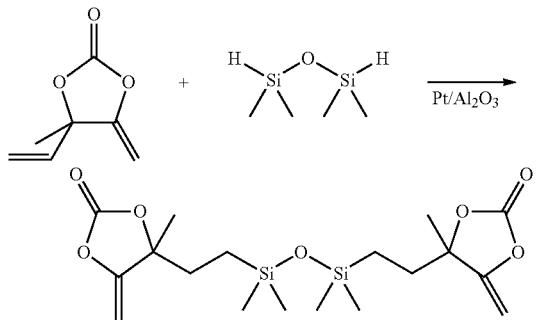

A 500 ml three-neck flask is charged under an argon atmosphere with 4-methyl-4-vinyl-5-methylene-1,3-dioxolan-2-one (210.6 g, 1.5 mol) and Pt/Al2O3 (5% Pt on Al203, 5.0 g, 1.3 mmol). The mixture is heated to 60° C. and then 1,1,3,3-tetramethyldisiloxane (95.06 g, 0.71 mol) is added in portions over the course of one hour. In this case an exothermic reaction with slight evolution of gas is observed (internal temperature climbs to 68° C.). After the end of the addition, the mixture is first stirred at 70° C. for 16 hours, then at 85-90° C. for 5 hours. After cooling to room temperature, the solidified reaction discharge is dissolved in 300 ml of toluene at 60° C. and the catalyst is removed hot by filtration. The toluene is removed under reduced pressure (50° C., 20 mbar) and the residue is dissolved in 1500 ml of n-hexane at 70° C., then cooled to 10° C. The colorless solid is isolated by filtration and washed with n-hexane (200 ml) and dried. The product is obtained as a colorless solid (222 g, 73%). GC purity: 99.6 area %; melting point: 80-82° C.

1H NMR (CDCl3, 500.1 MHz)=4.81 (d, br, 2H), 4.27(d, br, 2H), 1.81-1.87 (m, 2H), 1.64-1.70 (m, 2H), 1.58 (s, 6H), 0.48-0.61 (m, 4H), 0.07 (s, 12H).

13C NMR (CD2Cl2, 125.8 MHz)=157.8, 151.8, 88.5, 85.7, 34.9, 26.0, 11.2, 0.1. 29Si NMR (CDCl3, 99.4 MHz)= 8.1.

Besides the use of Pt/Al2O3 as catalyst, as described here, the following other Pt catalysts may also be employed: Pt/C and PtO2.

Preparation Example 3

Preparation of a Compound of Formula 1 from Crosslinker V58 and exoVCA (for Short: Si-V 2)

An autoclave is charged under an inert gas atmosphere with 4-methyl-4-vinyl-5-methylene-1,3-dioxolan-2-one (10.00 g, 0.07 mol), Pt/Al2O3 (5% Pt on Al2O3, 0.5 g) and Wacker® crosslinker V58 (46 g). The crosslinker V58 from Wacker comprises polysiloxane with a high number of silicon-bonded hydrogen atoms. The mixture is heated to 75° C. and stirred at this temperature for 10 hours. It is then cooled to room temperature and 1-hexene (100 ml) is added.

The mixture is stirred at 100° C. for 10 hours. After the solution has been filtered and the filtrate concentrated under reduced pressure (25 mbar, 50° C.), the product is obtained with a viscose consistency (55 g). It is used in the polymer synthesis without further purification and characterization. Characterization: the reaction was monitored by 1H NMR spectroscopy until the vinyl group signal characteristic of the reactant had disappeared.

Preparation Example 4

Preparation of a Compound of Formula 1 from Crosslinker V90 and exoVCA (for Short: Si-V 3)

A three-neck flask is charged under an inert gas atmosphere with 4-methyl-4-vinyl-5-methylene-1,3-dioxolan-2-one (10.0 g, 0.07 mol), Pt/Al2O3 (5% Pt on Al2O3, 0.5 g) and Wacker® crosslinker V90 (46 g). The crosslinker V90 from Wacker comprises polysiloxane with a high number of silicon-bonded hydrogen atoms. The mixture is heated to 85° C. and stirred at this temperature for 6 hours. It is then cooled to room temperature and 1-hexene (59 g) is added.

The mixture is stirred at 50° C. for 4 hours. After the solution has been filtered and the filtrate concentrated under reduced pressure (25 mbar, 50° C.), the product is obtained with a viscose consistency (49 g). It is used in the polymer synthesis without further purification and characterization.

Use Examples

1.) Coating Composition Comprising Si-V 1 and polyol.

10 g of Joncryl 500 (polyacrylatol), 4.14 g of Si-V 1, and 0.141 g of DBU (1,8-diazabicyclo[5.4.0]undec-7-ene, catalyst) were combined in 6 ml of butyl acetate and mixed at room temperature until the resulting mixture was uniform.

Joncryl® 500 is a commercially available polyacrylatol having a glass transition temperature Tg of −7° C., an OH number of 140 mg KOH/g, and an equivalent weight OH of 400 (this means:
1 mol OH to 400 g of the polyacrylatol)
Joncryl 500 is in the form of an 80% strength by weight solution in MAK.

The resulting mixture was applied with a wet film thickness of 250 μm to the respective substrate (glass for determining the hardness, and Bonder panel (Gardobond®) for determining the elasticity and the adhesion (cross-cut)), left to evaporate at room temperature for 15 minutes, and then cured for 30 minutes in a drying oven at the stated temperature (see Table 1). For subsequent crosslinking, the cured film was stored overnight in a conditioning chamber, after which the typical paint parameters were ascertained.

The Erichsen cupping was determined in analogy to DIN 53156 by the pressing of a metal ball into the uncoated side of the panel. High values denote high flexibility. The value determined is the value at which the coating exhibits the first crack.

The pendulum damping was determined in accordance with DIN 53157 on glass. High values denote high hardness.

The cross-cut test (G for short) tests the adhesion. The test took place likewise on Bonder panel. In the cross-cut test, the surface of the cured paint is incised with a lattice and observed to determine whether the paint undergoes delamination at the incision edges. Delamination is assessed visually with the scores of 0 (no delamination) to 5 (marked delamination). The lower the score, the better the adhesion.

The results of the performance tests are found in Table 1.

TABLE 1

| Example | Pendulum hardness [sec] | Erichsen cupping [mm] | Appearance | G | Curing at [° C./min] |
|---------|------------------------|----------------------|--------------|---|----------------------|
| 1       | 18                     | >9.5                 | clear, specks | 0 | 100° C.              |
| 2       | 18                     | >9.5                 | clear, specks | 0 | 120° C.              |
| 3       | 18                     | >9.5                 | clear, specks | 0 | 140° C.              |

2.) Coating Composition comprising Si-V 3 and polyol.

Joncryl® 945 is a commercially available polyacrylatol having a glass transition temperature Tg of 17° C., an OH number of 180 mg KOH/g, and an OH equivalent weight of 310 (this means: 1 mol OH to 310 g of the polyacrylatol)

Joncryl 945 is in the form of a 76% strength by weight solution in n-butyl acetate.

Sovermol 8151® is a commercially available biobased polyol having an OH equivalent weight of 260.

Desmophen 650 MPA® is a commercially available branched polyester from Bayer MaterialScience, having a solids content of 65 wt % in MPA (1-methoxypropyl acetate). The hydroxyl group content is reported as 5.3 wt %.

For the determination of the pot life, Si-V 3, the respective polyol (Table 2), and DBU as catalyst were mixed in the quantities indicated, and a determination was made of the time after which there was a marked increase in viscosity and the mixture was no longer fluid.

TABLE 2

| | Pot lives | | | |
|---|---|---|---|---|
| Example | Polyol Type and amount | Si—V3 [g] | Catalyst DBU [g] | Pot life [min] |
| 4  | Joncryl 500; 2.5 g       | 4.0 | 0.035   | 20   |
| 5  | Joncryl 945; 2.0 g       | 4.0 | 0.035   | 20   |
| 6  | Joncryl 500; 1.25g       | 2.0 | 0.00875 | 45   |
| 7  | Joncryl 945; 1.0 g       | 2.0 | 0.00875 | 35   |
| 8  | Desmophen 650 MPA; 0.8 g | 2.0 | 0.00875 | >120 |
| 9  | Sovermol 815; 0.65 g     | 2.0 | 0.00875 | 30   |
| 10 | Joncryl 500; 1.25 g      | 2.0 | 0.00583 | >120 |
| 11 | Joncryl 945; 1.0 g       | 2.0 | 0.00583 | >120 |
| 12 | Desmophen 650 MPA; 0.8 g | 2.0 | 0.00583 | >120 |
| 13 | Sovermol 815; 0.65 g     | 2.0 | 0.00583 | >120 |

3.) Coating Composition Comprising Si-V 2 and amines 4.61 g of Si-V 2 were mixed with 0.2 g of isophoronediamine (IPDA) and 0.28 g of Jeffamine D 230® until the resulting mixture was uniform. No accompanying catalyst was used.

For the determination of the performance properties, the resulting mixture was applied as described above to glass or Bonder panel in a wet film thickness of 250 μm, left to evaporate at room temperature for 15 minutes, and then cured for 2×60 minutes in a drying oven at 100° C. For subsequent crosslinking, the cured film was stored overnight in a conditioned chamber, after which the typical paint parameters were ascertained.

Jeffamine D 230® is a commercially available polyetheramine from Huntsman, as diamine. (The manufacturer reports Jeffamine D 230 to have a weight-average molar weight of 230 and an average number of 2.5 repeating propylene glycol units).

With regard to performance tests, the details stated above are applicable. In addition the chemical resistance was tested.

The test for resistance to exposure to chemicals was carried out in a method based on DIN 68861-1, using a 1:1 mixture of ethanol and ethyl acetate and an exposure time of 10 seconds. The damage to the paint surface was assessed visually with the scores of 0 (no damage) to 5 (paint dissolves and can be wiped away). The lower the score, the better the resistance toward chemicals.

The results of the performance tests are found in Table 3.

| Example | Chemicals test | Pendulum hardness [sec] | Erichsen cupping [mm] | Appearance, comments | G |
|---|---|---|---|---|---|
| 14 | 0 | 32 | 7.8 | Smooth, 53 μm film thickness | 0 |

Si-V 2 was mixed with various amines and the pot lives were determined as described above.

The amines used are m-xylenediamine (MXDA), isophoronediamine (IPDA), Jeffamine D 230, or mixtures thereof. The amines were used in different molar ratios to the Si-V 2.

Results are found in Table 4.

TABLE 4

| | | Pot lives | |
|---|---|---|---|
| Example | Amine Type and amount | Si—V2 [g] | Pot life [min] |
| 15 | IPDA; 0.34 g | 3.09 | <5 |
| 16 | MXDA; 0.28 g | 3.20 | 0 |
| 17 | Jeffamine D 230; 0.48 g | 3.19 | 20 |
| 18 | IPDA; 0.23 g | 2.63 | <5 |
| 19 | MXDA; 0.12 g | 2.76 | 0 |
| 20 | Jeffamine D 230; 0.38 g | 3.07 | 15 |
| 21 | IPDA; 0.20; Jeffamine D 230; 0.28 g | 4.61 | 5 |

The invention claimed is:

1. A coating composition, comprising:
a carbonate compound of formula III

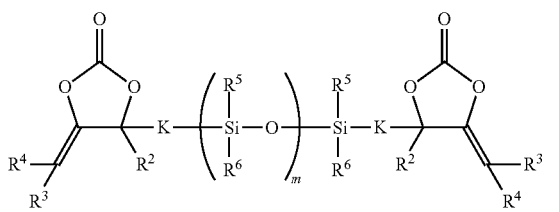

formula III wherein $R^2$ to $R^4$ are independently hydrogen or an organic group comprising 1 to 10 C atoms, K is a divalent organic group comprising 2 to 10 C atoms, $R^5$ and $R^6$ are independently a hydrogen atom or an organic group comprising 1 to 10 C atoms, and m is an integer of from 1 to 99.

2. The coating composition according to claim 1, which comprises from 0.1 to 50 wt% of the carbonate compound.

3. The coating composition according to claim 1, further comprising:
a reactive compound comprising at least two reactive groups selected from the group consisting of a hydroxyl group, a primary amino group, a secondary amino group, and a mercapto group.

4. The coating composition according to claim 3, wherein the reactive compound comprises a polyester polyol, a polyether polyol, a polyesteramide polyol, a polycarbonate polyol, a polyacrylate polyol, a polyetheramine, a polyamidoamine, or any mixture thereof.

5. A method for producing a coated substrate, the method comprising:
applying a coating composition to a substrate, wherein the coating composition comprises
a carbonate compound comprising at least two cyclic carbonate groups and a siloxane group,
a reactive compound comprising at least two reactive groups selected from the group consisting of a hydroxyl group, a primary amino group, a secondary amino group, and a mercapto group, and
thereafter reacting the carbonate compound with the reactive compound.

6. A coating composition, comprising:
a carbonate compound comprising at least two cyclic carbonate groups and a siloxane group,
wherein the carbonate compound is obtained by hydrosilylation of a compound of formula IV

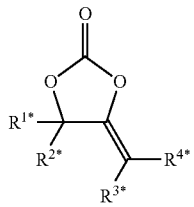

formula IV wherein radicals R1* to R4* are independently hydrogen or an organic group comprising 1 to 10 C atoms, but at least one of the radicals R1* to R4* comprises an ethylenically unsaturated group with a siloxane which comprises at least two silicon-bonded hydrogen atoms.

7. The coating composition according to claim 6, wherein the compound of the formula IV is a compound in which $R^{1*}$ is a C2 to C10 alkenyl group or a C2-C10 alkynyl group, and $R^{2*}$, $R^{3*}$ and $R^{4*}$ are independently a hydrogen atom or a C1 to C10 alkyl group.

8. The coating composition according to claim 6, wherein $R^{1*}$ in the formula IV is a vinyl group.

9. The coating composition according to claim 6, wherein the compound of the formula IV is a compound in which $R^{1*}$ is a vinyl group, $R^{2*}$ is a C1 to C4 alkyl group, and $R^{3*}$ and $R^{4*}$ are an H atom.

10. The coating composition according to claim 6, which comprises from 0.1 to 50 wt % of the carbonate compound.

11. The coating composition according to claim 6, further comprising:
a reactive compound comprising at least two reactive groups selected from the group consisting of a hydroxyl group, a primary amino group, a secondary amino group, and a mercapto group.

12. The coating composition according to claim 11, wherein the reactive compound comprises a polyester polyol, a polyether polyol, a polyesteramide polyol, a polycarbonate polyol, a polyacrylate polyol, a polyetheramine, a polyamidoamine, or any mixture thereof.

13. A coating composition, comprising
a carbonate compound comprising at least two cyclic carbonate groups and a siloxane group, and
a reactive compound comprising at least two reactive groups selected from the group consisting of a hydroxyl group, a primary amino group, a secondary amino group, and a mercapto group; and
wherein the reactive compound comprises a polyester polyol, a polyether polyol, a polyesteramide polyol, a polycarbonate polyol, a polyacrylate polyol, a polyetheramine, a polyamidoamine, or any mixture thereof.

14. The coating composition according to claim 13, wherein the carbonate compound comprises from two to fifty cyclic carbonate groups and a siloxane group comprising 2 to 100 silicon atoms.

15. The coating composition according to claim 13, wherein the carbonate compound is a compound of formula III

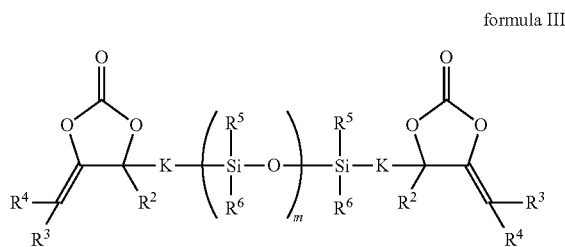

formula III wherein $R^2$ to $R^4$ are independently hydrogen or an organic group comprising 1 to 10 C atoms, K is a divalent organic group comprising 2 to 10 C atoms, $R^5$ and $R^6$ are independently a hydrogen atom or an organic group comprising 1 to 10 C atoms, and m is an integer of from 1 to 99.

16. The coating composition according to claim 13, wherein the carbonate compound is obtained by hydrosilylation of a compound of formula IV

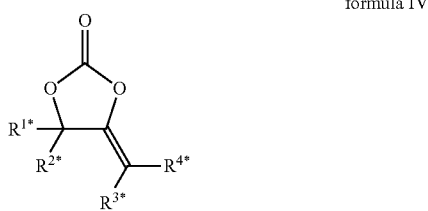

formula IV wherein radicals R1* to R4* are independently hydrogen or an organic group comprising 1 to 10 C atoms, but at least one of the radicals R1* to R4* comprises an ethylenically unsaturated group with a siloxane which comprises at least two silicon-bonded hydrogen atoms.

17. The coating composition according to claim 16, wherein the compound of the formula IV is a compound in which $R^{1*}$ is a C2 to C10 alkenyl group or a C2-C10 alkynyl group, and $R^{2*}$, $R^{3*}$ and $R^{4*}$ are independently a hydrogen atom or a C1 to C10 alkyl group.

18. The coating composition according to claim 16, wherein $R^{1*}$ in the formula IV is a vinyl group.

19. The coating composition according to claim 16, wherein the compound of the formula IV is a compound in which $R^{1*}$ is a vinyl group, $R^{2*}$ is a C1 to C4 alkyl group, and $R^{3*}$ and $R^{4*}$ are an H atom.

20. The coating composition according to claim 13, which comprises from 0.1 to 50 wt % of the carbonate compound.

21. A carbonate compound of formula III

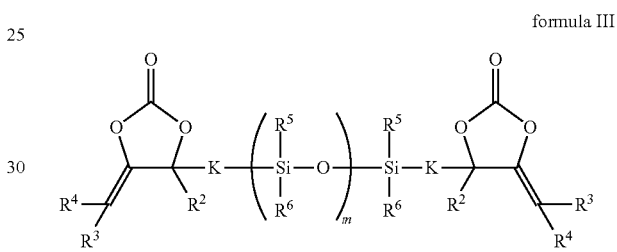

formula III wherein $R^2$ to $R^4$ are independently hydrogen or an organic group comprising 1 to 10 C atoms, K is a divalent organic group comprising 2 to 10 C atoms, $R^5$ and $R^6$ are independently a hydrogen atom or an organic group comprising 1 to 10 C atoms, and m is an integer of from 1 to 99.

* * * * *